US008530507B2

(12) United States Patent
Wang et al.

(10) Patent No.: US 8,530,507 B2
(45) Date of Patent: Sep. 10, 2013

(54) USE OF LEVO-ORNIDAZOLE IN THE PREPARATION OF ANTI-ANAEROBIC BACTERIA INFECTION DRUGS

(75) Inventors: Yong Wang, Jiangsu (CN); Cang Zhang, Jiangsu (CN); Zaijin Teng, Jiangsu (CN); Li Li, Jiangsu (CN)

(73) Assignee: Nanjing Sanhome Pharmaceutical Co., Ltd., Jiangsu (CN)

( * ) Notice: Subject to any disclaimer, the term of this patent is extended or adjusted under 35 U.S.C. 154(b) by 1081 days.

(21) Appl. No.: 11/909,062

(22) PCT Filed: Apr. 17, 2006

(86) PCT No.: PCT/CN2006/000688
§ 371 (c)(1),
(2), (4) Date: Feb. 13, 2008

(87) PCT Pub. No.: WO2006/114042
PCT Pub. Date: Nov. 2, 2006

(65) Prior Publication Data
US 2009/0326030 A1 Dec. 31, 2009

(30) Foreign Application Priority Data
Apr. 28, 2005 (CN) .......................... 2005 1 0068478

(51) Int. Cl.
*A61K 31/415* (2006.01)
*A61K 9/20* (2006.01)
*A61K 9/00* (2006.01)

(52) U.S. Cl.
USPC ............................ 514/398; 424/400; 424/464

(58) Field of Classification Search
USPC .................. 514/398; 424/464, 400
See application file for complete search history.

(56) References Cited

U.S. PATENT DOCUMENTS
3,435,049 A * 3/1969 Hoffer ........................ 548/330.1

FOREIGN PATENT DOCUMENTS
| CN | 1400312 | 3/2003 |
|----|---------|--------|
| CN | ZL02136622.5 | 7/2005 |
| CN | 168116 | 10/2005 |
| CN | 173905 | 3/2006 |
| CN | 1739504 | 3/2006 |

OTHER PUBLICATIONS

Remington's Pharmaceutical Sciences, Seventeenth Edition, 1985, pp. 1542-1543.*
China Pharmacy, 2003, vol. 14 No. 1, Tian Huaiping et al. "The pharmacological effect and clinical application of ornidazole", pp. 50-51.
China Pharmacy, 2003, vol. 14 No. 1, Tian Huaiping et al. "The pharmacological effect and clinical application of ornidazole"—Abstract.

* cited by examiner

*Primary Examiner* — Shengjun Wang
(74) *Attorney, Agent, or Firm* — McDonnell Boehnen Hulbert & Berghoff LLP

(57) ABSTRACT

The use of levo-ornidazole in the preparation of medicine for preventing and treating the anti-anaerobic bacteria infection is provided. It is demonstrated that levo-ornidazole exhibits lower toxicity and less central inhibition effects than dextro-ornidazole or racemic ornidazole. L-ornidazole possesses pharmacokinetics characteristics, which are superior to that of the racemic ornidazole, and anti-anaerobic activities which are slightly better than or substantially the same as that of the racemic ornidazole. Also, this invention particularly relates to a preparation process, which comprises formulating L-ornidazole as anti-anaerobic infection pharmaceutical preparations, which are suitable for clinical uses.

5 Claims, No Drawings

USE OF LEVO-ORNIDAZOLE IN THE PREPARATION OF ANTI-ANAEROBIC BACTERIA INFECTION DRUGS

FIELD OF THE INVENTION

This invention relates to the use of Levo-ornidazole in the preparation of a medicament for preventing and treating anti-anaerobic bacteria infection, and particularly to a pharmaceutical preparation formulated from L-ornidazole suitable for clinical use, which includes oral preparation and intravenous preparation.

BACKGROUND OF THE INVENTION

Levo-ornidazole (1-(3-chloro-2-S-(−)-hydroxypropyl)-2-methyl-5-nitroimidazole) is the levo-isomer of ornidazole (CAS 16773-42-5). As a nitroimidazole derivative, ornidazole is a powerful anti-anaerobic bacteria and anti-parasite infection agent, and also as the newly developed third-generation of nitroimidazole derivative next to the 2-methyl-5-nitro-1H-Imidazole-1-ethanol, ornidazole exhibits higher therapeutical efficacy, shorter clinical course, better tolerance, and wider in-vivo distribution. The anti-microorganisms effect of ornidazole is promoted by the reduction of nitro group of its molecule to amino group under anaerobic environment, or by the formation of free radical followed by interaction with the cellular components, and caused to the death of microorganisms. Ornidazole racemate is the active ingredient in commercial ornidazole agents. Anti-anaerobic bacteria activity of ornidazole has been widely reported in clinical practice, such as the clinical and experimental study of ornidazole for the treatment of oral anaerobic infections (see Chinese Journal of Nosocomiology. 2004. 14 (3). -325-327); the clinical effects of ornidazole injection in the treatment of gynecological anaerobic infections (see Chinese Journal of New Drugs. 2004. 13 (2).-158-160); analysis of ornidazole injection in the treatment of 56 cases of senile diabetic foot anaerobic infections (the Chinese Medical Journal Writing. 2004. 11 (10).-843-844). Ornidazole exhibits good therapeutical efficacy in the treatment of anaerobic bacteria infections, but there are also some adverse effects, primarily expressed as central Inhibitory effects. In China, there is a patent application (CN 1400312A) regarding the separation of racemic ornidazole into L- and D-ornidazole by means of enzymatic resolution, however, comparative studies on the pharmacology and pharmacodynamics among L- and D-ornidazole and racemic ornidazole has not been published yet.

DISCLOSURE OF THE INVENTION

Clinical use of ornidazole shows that ornidazole is effective in treating anaerobic bacteria infections, but some adverse reactions are also reported. In order to maintain and enhance the therapeutical efficacy, and minimize the adverse effects, research studies were conducted on L-ornidazole with respect to its pharmacokinetics, pharmacodynamics, toxicology and general pharmacology, in which L-ornidazole is found having pharmacokinetics characteristics superior to D-ornidazole and racemic ornidazole, and also having central nervous system toxicity lower than D-ornidazole and racemic ornidazole. For these reasons, it would be more practicable to formulate L-ornidazole as anti-anaerobic bacteria infection drugs for clinical uses.

The present invention determines that L-ornidazole has more practicability in the preparation of anti-anaerobic bacteria infection drugs by the following experiments.

(I) Toxicology Test of L-Ornidazole

1. Acute Toxicology Test of L-ornidazole

Kunming mice, half males and half females, with body weights of 18~22 g, were administered the testing drug solution by injection 8 hours after fasting. The death status of animals was consecutively observed for 14 days after administration.

1) Determination of $LD_{50}$ (Half Lethal Dose) of Intravenous Injection in Mice

TABLE 1

$LD_{50}$ and 95% confidence interval (CI) of intravenous injection of L-ornidazole in mice (Bliss Method)

| Dose (mg/kg) | log dose | Number of animals | Number of dead animals | Death rate (%) | Probability units (Y) | $LD_{50}$ and CI (mg/kg) |
|---|---|---|---|---|---|---|
| 370 | 2.568 | 10 | 10 | 100 | 6.38 | 332 (312-352) |
| 333 | 2.522 | 10 | 3 | 30 | 5.05 | |
| 300 | 2.477 | 10 | 2 | 20 | 3.72 | |
| 270 | 2.431 | 10 | 0 | 0 | 3.04 | |
| 243 | 2.385 | 10 | 0 | 0 | 1.06 | |

TABLE 2

$LD_{50}$ and 95% confidence interval (CI) of intravenous injection of racemic ornidazole in mice (Bliss Method)

| Dose (mg/kg) | log dose | Number of animals | Number of dead animals | Death rate (%) | Probability units (Y) | $LD_{50}$ and CI (mg/kg) |
|---|---|---|---|---|---|---|
| 370 | 2.568 | 10 | 10 | 100 | 6.57 | 306 (272-346) |
| 333 | 2.522 | 10 | 5 | 50 | 5.73 | |
| 300 | 2.477 | 10 | 5 | 50 | 4.90 | |
| 270 | 2.431 | 10 | 3 | 30 | 4.06 | |
| 243 | 2.385 | 10 | 0 | 0 | 3.22 | |

2) Determination of $LD_{50}$ of Intraperitoneal Injection in Mice

TABLE 3

$LD_{50}$ and 95% confidence interval (CI) of intraperitoneal injection of L-ornidazole in mice (Bliss method)

| Dose (mg/kg) | log dose | Number of animals | Number of dead animals | Death rate (%) | Probability units (Y) | $LD_{50}$ and CI (mg/kg) |
|---|---|---|---|---|---|---|
| 2000 | 3.301 | 10 | 10 | 100 | 7.13 | 1378 (1244-1526) |
| 1700 | 3.230 | 10 | 9 | 90 | 6.17 | |
| 1445 | 3.160 | 10 | 6 | 60 | 5.20 | |
| 1228 | 3.089 | 10 | 3 | 30 | 4.24 | |
| 1044 | 3.019 | 10 | 0 | 0 | 3.27 | |

TABLE 4

$LD_{50}$ and 95% confidence interval (CI) of intraperitoneal injection of racemic ornidazole in mice (Bliss Method)

| Dose (mg/kg) | log dose | Number of animals | Number of dead animals | Death rate (%) | Probability units (Y) | $LD_{50}$ and CI (mg/kg) |
|---|---|---|---|---|---|---|
| 1700 | 3.230 | 10 | 10 | 100 | 7.52 | 1115 (1026-1212) |
| 1445 | 3.160 | 10 | 10 | 100 | 6.49 | |
| 1228 | 3.089 | 10 | 8 | 80 | 5.46 | |
| 1044 | 3.019 | 10 | 3 | 30 | 4.42 | |
| 887.4 | 2.948 | 10 | 0 | 0 | 3.39 | |

3) Determination of $LD_{50}$ of Oral Gavage in Mice

TABLE 5

$LD_{50}$ and 95% confidence interval (CI) of oral gavage of L-ornidazole in mice (Bliss method)

| Dose (mg/kg) | log dose | Number of animals | Number of dead animals | Death rate (%) | Probability units (Y) | $LD_{50}$ and CI (mg/kg) |
|---|---|---|---|---|---|---|
| 1600 | 3.204 | 10 | 10 | 100 | 6.96 | |
| 1280 | 3.107 | 10 | 8 | 80 | 5.86 | 1069 (935.3-1221) |
| 1024 | 3.010 | 10 | 4 | 40 | 4.86 | |
| 819.2 | 2.913 | 10 | 1 | 10 | 3.86 | |
| 655.4 | 2.817 | 10 | 0 | 0 | 2.87 | |

TABLE 6

$LD_{50}$ and 95% confidence interval (CI) of intraperitoneal administration of racemic ornidazole in mice (Bliss Method)

| Dose (mg/kg) | log dose | Number of animals | Number of dead animals | Death rate (%) | Probability units (Y) | $LD_{50}$ and CI (mg/kg) |
|---|---|---|---|---|---|---|
| 1600 | 3.107 | 10 | 10 | 100 | 7.19 | 769.4 (674.2-878.0) |
| 1280 | 3.010 | 10 | 9 | 90 | 6.19 | |
| 1024 | 2.913 | 10 | 7 | 70 | 5.19 | |
| 819.2 | 2.817 | 10 | 2 | 20 | 4.20 | |
| 655.4 | 2.720 | 10 | 0 | 0 | 3.20 | |

From the studies on acute toxicology, it shows that in the case of administration of L-ornidazole in mice, $LD_{50}$ was 332 mg/kg (95% CI: 312~362 mg/kg) for intravenous injection, 1378 mg/kg (95% CI: 1244~1526 mg/kg) for intraperitoneal injection and 1069 mg/kg (95% CI: 935.3~1222 mg/kg) for oral gavage. In the case of racemic ornidazole, $LD_{50}$ was 306 mg/kg (95% CI: 272~346 mg/kg) for intravenous injection, 1115 mg/kg (95% CI: 1026~1212 mg/kg) for intraperitoneal injection and 769.4 mg/kg (95% CI: 674.2~878.0 mg/kg) for oral gavage. In accordance with the above results, it was demonstrated that L-ornidazole exhibited lower toxicity and relatively higher safety as compared with the racemic ornidazole.

2. Toxicity Test in Beagle Dogs (Non-Rodent) After Intravenous Administration of L-ornidazole for Two Weeks Beagle dogs, 4 dogs in each group with half females and half males, were divided into L-, D-, and racemic ornidazole groups.

It was demonstrated that significant toxic effects were not observed in beagle dogs receiving 200 mg/kg (corresponding to 8 times of human dose calculated according to body weights) of L-ornidazole by intravenous infusion using infusion pump. The manifestations of this kind of administration were merely drooling, vomiting, involuntary urination and the like, and recovered in 1-2 hours. Food intake of testing animals was inhibited while body weight of the testing animals was inhibited to a certain extent. Significant pathological changes were not found in the histological examination of organs.

Beagle dogs who received 200 mg/kg D-ornidazole by intravenous infusion using infusion pump exhibited toxicity and side effects such as drooling, vomiting, myasthenia of limbs, astasia, hyperspasmia. With the increased times of administration, the above-mentioned toxicity and side effects became more significant and the recovery time was also longer. Food intake and body weight of the testing animals were significantly inhibited. In accordance with the result of the histological examination, organs of the D-ornidazole group animals have normal structure and significant pathological changes were not observed. The structure of the cerebellum was clear, but the number of Purkinje cells was significantly reduced as compared with the L- and racemic ornidazole group, and mild cellular degeneration was observed.

Beagle dogs who received 200 mg/kg racemic ornidazole by intravenous infusion using infusion pump exhibited similar toxicity and side effects as D-ornidazole, but to a less extent. No reduction in the number of Purkinje cells and cellular degeneration was observed in cerebellum in the histological examination.

The results showed that, among the three ornidazoles, L-ornidazole exhibited the least toxicity and side effects such as inhibition of food intake and body weight, and racemic ornidazole was the next while D-ornidazole was the most severe one and they were of statistically significance. In addition, observable cellular degeneration was found in cerebellum in the D-ornidazole group.

In accordance with the above results, it was demonstrated that L-ornidazole exhibited lower central nervous system toxicity and relatively higher safety as compared with D- and racemic ornidazole.

(II) Pharmacodynamic Studies of L-Ornidazole

1. In Vitro Pharmacodynamic Studies of L-ornidazole

Experimental strains: isolated from clinical specimens, and species identification were conducted.

Bacilli preparation: 4~5 bacteria colonies with same pattern selected from anaerobic GAM plate were inoculated in GAM broth with inoculating loop. The bacteria was incubated at 35° C. under anaerobic condition until a slight turbidity was attained, and adjusted by means of sterilized saline (deoxygenated) so as to attain a turbidity equivalent to the No. 0.5 McFarland turbidity tube, then diluted with GAM broth (at 1:200) for later use.

MIC (Minimum Inhibitory Concentration) determination: the testing drugs and control drugs were diluted with GAM broth to different concentrations in the test tubes, followed by addition of equal volume of diluted Bacilli (at 1:200), MIC values were read 72 hours after anaerobic incubation at 35° C.

MBC (minimum bactericidal concentration): upon reading the MIC results, 0.1 ml culture was collected respectively from the tubes, where growth was not happened, and the culture was then placed on a sterilized GAM agar plate, and allowed to undergo incubation at 35° C. under anaerobic condition for another 72 hours. A concentration with less than 5 five colonies on the plate was considered as MBC.

Racemic ornidazole was used as the positive control drug, because the control drug and the testing drug belong to the same anti-anaerobic bacteria drug category.

The results are shown in table 7.

TABLE 7

The MIC values (mg/L) of 117 experimental strains with the testing drug and the control drug

| Bacteria | Number of Strains | Testing drug (L-ornidazole) | | | Control drug (Racemic ornidazole) | | |
|---|---|---|---|---|---|---|---|
| | | MIC50 | MIC90 | Range | MIC50 | MIC90 | Range |
| *Bacteroides* | 40 | 4.0 | 8.0 | 20~16.0 | 4.0 | 8.0 | 2.0~16.0 |
| *Peptostreptococcus* | 35 | 4.0 | 8.0 | 2.0~32.0 | 4.0 | 8.0 | 2.0~>32.0 |
| *Veillonella* | 23 | 4.0 | 8.0 | 2.0~8.0 | 4.0 | 8.0 | 2.0~16.0 |
| *Fusobacterium nucleatum* | 11 | 2.0 | 16.0 | 1.0~16.0 | 2.0 | 32.0 | 1.0~32.0 |
| *Clostridium* | 6 | 2.0 | 2.0 | 1.0~2.0 | 2.0 | 2.0 | 1.0~2.0 |
| *Porphyromonas gingivalis* | 2 | | | 2.0, 2.0 | | | 2.0, 2.0 |

The in vitro pharmacodynamic studies showed that activity against various anaerobic bacteria of L-ornidazole and racemic ornidazole were substantially the same.

2. In Vivo Pharmacodynamic Studies of L-Ornidazole

Kunming white mice, body weight of 20±2 g, half males and half females. 10 mice in each dose group with half females and half males. Abdominal infection models were prepared with the entire animal (mice) and treatments were conducted with the testing drugs. The therapeutical efficacy was observed and expressed as $ED_{50}$ (half effective dose). Drugs were administered twice by oral gavage (administered immediately after infection for one and 6 hours after infection for the other one). The death status of animals was observed consecutively for seven days after infection and being treated.

From the results, it was shown that in the case of antibacteroides (including *Escherichia coli*) infection, the value of $ED_{50}$ was 31.0 mg/kg (95% CI: 43.3~22.2) for L-ornidazole, and 39.9 mg/kg (95% CI: 51.9~30.7) for racemic ornidazole. In the case of anti-peptostreptococcus (including *Escherichia coli*), the $ED_{50}$ was 42.0 mg/kg (95% CI 50.9~34.6) for L-ornidazole, and 49.1 mg/kg (95% CI 61.1~39.4) for racemic ornidazole. It was demonstrated that in vivo anti-anaerobic activities of L-ornidazole was slightly better than or substantially the same as that of racemic ornidazole.

Pharmacodynamic studies showed that antibacteria activity of L-ornidazole against various anaerobic bacteria is slightly better than or substantially the same as that of racemic ornidazole.

(III) In Vivo Pharmacokinetics Studies of L-Ornidazole

The clinical dose of ornidazole is 500 mg for human. By calculating, based on body surface area, the pharmacokinetic experimental dose in Beagle dogs was 13 mg/kg in vivo.

Six adult beagle dogs (half males and half females, body weight of 9~11.5 kg) were randomly divided into three groups. According to crossover design, intravenous injection of L-, D-, and racemic ornidazole were administered in turn to each dog every other week (with one week washout period in between). 2 ml of blood was collected from the vein located at the forelimb of the dogs before drug administration and 0.083, 0.5, 1.0, 2.0, 4.0, 6.0, 8.0, 12.0, 16.0, 24.0 hours after drug administration, which was then placed in the heparinized tube, followed by centrifugation to obtain the plasma. Plasma concentration of drug was determined by HPLC.

Pharmacokinetics parameters were estimated using the non-compartmental models. The corresponding pharmacokinetics parameters were obtained by BAPP2.0 using the data of plasma concentration of blood with time obtained above.

The results showed that after administration of individual intravenous dose of L-, D-, and racemic ornidazole to beagle dogs, their $t_{1/2}$ (half life) were 6.97±1.09 hours, 6.06±2.29 hours and 5.55±3.12 hours respectively; $AUC_{0-t}$ (area under curve) were 90.94±8.33 µg·hour/ml, 66.57±10.51 µg·hour/ml and 76.72±10.75 µg·hour/ml respectively; MRT (mean retention time of drugs) were 10.06±1.57 hours, 8.74±3.30 hours and 8.01±3.42 hours respectively; Cl (clearance) were 1.22±0.13 L/hour, 1.59±0.28 L/hour and 1.43±0.27 L/hour respectively; $V_\beta$ (elimination volume of distribution) were 12.23±1.84 L, 13.59±4.99 L and 11.17±3.96 L respectively. It was demonstrated from the above results that in vivo clearance of D-ornidazole was slightly faster than L-ornidazole, and as a result, the concentration of L-ornidazole was higher than D-ornidazole in the elimination phase, which render the significant difference in AUC between the L- and D-ornidazole. There was no significant difference in other pharmacokinetics parameters between L- and D-ornidazole using t-test, which implied that they had similar in vivo pharmacokinetics activities. From the viewpoint of pharmacokinetics, L-ornidazole was superior to the D-ornidazole in terms of its pharmacokinetic behavior. After administration by intravenous injection, in vivo transformation of enantiomers between L- and D-ornidazole was not occurred. Significant in vivo pharmacokinetics interactions were not observed between L- and D-ornidazole as well. In addition, in vivo plasma concentration of drug and pharmacokinetic parameters of L- and D-ornidazole determined from using chiral chromatography was substantially the same as that determined from using non-chiral chromatography. The elimination rate of L-ornidazole was slower than that of D-ornidazole as determined by either method.

(IV) General Pharmacology

Effects of L-, D- and racemic ornidazole on mental nervous system in mice were studied.

(1) Effects of L-Ornidazole on Spontaneous Activities in Mice

Mice weighed 18~22 g, half males and half females, were divided into 9 administration groups and 10 mice in each group, where doses of 40, 80 and 160 mg/kg of L-, D- and racemic ornidazole were administered to them by intravenous injection 8 hours after fasting. Chlorpromazine was administered at dose of 3 mm/kg in the positive control group, and the same volume of propylene glycol containing 0.9% sodium chloride injection was administered in the vehicle control group. Spontaneous activity was recorded at 0.5, 1, 2, 3 and 4 hours after drug administration. The injection volume was 0.2 ml/10 g and the administration rate was 0.2 ml/10 sec.

The results showed that at a dose of 160 mg/kg, as compared with the vehicle control group, spontaneous activity was reduced significantly at 0.5, 1 and 2 hours after administration of L-ornidazole, and the condition gradually become normal after 3 hours. Spontaneous activity was reduced significantly at 0.5, 1, 2, 3 and 4 hours after administration of D-ornidazole as compared with the vehicle control group, and the condition was not recovered in 4 hours. Spontaneous activity was reduced significantly at 0.5, 1, 2 and 3 hours after administration of racemic ornidazole as compared with the vehicle control group, and the condition gradually become normal after 4 hours. At a dose of 160 mg/kg, L- and D-ornidazole had significant difference in spontaneous activity at 0.5, 1, 2, 3 and 4 hours after drug administration. L- and racemic ornidazole had significant difference in spontaneous activity at 1, 2 and 3 hours after drug administration. The results showed that at a dose of 160 mg/kg, L-ornidazole exhibited less inhibitory effect on the spontaneous activity in mice than D- or racemic ornidazole.

At a dose of 80 mg/kg, as compared with the vehicle control group, spontaneous activity was reduced significantly at 0.5 and 1 hour after administration of L-ornidazole and the condition gradually become normal after 2 hours. Spontaneous activity was reduced significantly at 0.5, 1, 2, 3 and 4 hours after administration of D-ornidazole as compared with the vehicle control group, and the condition was not recovered in 4 hours. Spontaneous activity was reduced significantly at 0.5, 1 and 2 hours after administration of racemic ornidazole as compared with the vehicle control group, and the condition gradually become normal after 3 hours. At a dose of 80 mg/kg, L- and D-ornidazole had significant difference in spontaneous activity at 0.5, 1, 2, 3 and 4 hours after drug administration. L- and racemic ornidazole had no significant difference in spontaneous activity. The results showed that at a dose of 80 mg/kg, L-ornidazole exhibited less inhibitory effect on the spontaneous activity in mice than D-ornidazole.

At a dose of 40 mg/kg, as compared with the vehicle control group, significant reduction in spontaneous activity was not observed after administration of L-ornidazole. Spontaneous activity was reduced significantly at 0.5, 1 and 2 hours after administration of D-ornidazole as compared with the vehicle control group, and the condition gradually become normal after 3 hours. Spontaneous activity was reduced significantly 1 hour after administration of racemic ornidazole as compared with the vehicle control group, and the condition gradually become normal after 2 hours. At a dose of 40 mg/kg, L- and D-ornidazole had significant difference in spontaneous activity at 0.5, 1 and 2 hours after drug administration. L- and racemic ornidazole had no significant difference in spontaneous activity. The results showed that at a dose of 40 mg/kg, L-ornidazole exhibited less inhibitory effect on the spontaneous activities in mice than D-ornidazole.

(2) Hypnotic Effect of Intravenous Injection of L-Ornidazole in Mice

White mice, half males and half females, fasted for eight hours. The disappearance of righting reflex in mice was observed. The number of animals who lost their righting reflex was recorded in 30 minutes after drug administration. The injection volume was 0.2 ml/10 g; the administration rate was 0.2 ml/10 sec.

No loss in righting reflex was observed in mice who received individual dose of 40 or 80 mg/kg of L-, D- and racemic ornidazole. They were merely manifested in reduction in activities and sedation.

No loss in righting reflex was observed in mice who received individual dose of 160 mg/kg of L-ornidazole. However, 10 and 6 mice was observed with loss in righting reflex in the D-ornidazole group and racemic ornidazole group respectively, which showed significant difference from L-ornidazole.

(3) The Effect of Intravenous Injection of L-Ornidazole on the Hypnotic Effect Induced by Sodium Thiopental in Mice White mice, half males and half females, were divided into 6 administration groups and 10 mice in each group, where dose of 40 and 80 mg/kg of L-, D- and racemic ornidazole were administered to them 8 hours after fasting. The same volume of 0.9% sodium chloride injection containing propylene glycol was administered in the vehicle control group. 30 minute after drug administration, 40 mg/kg of sodium thiopental was administered to mice by intraperitoneal injection. The time for the loss of righting reflex and the time for the recovery were recorded. The injection volume was 0.2 ml/10 g, the administration rate was 0.2 ml/10 sec.

The results showed that at a dose of 40 mg/kg, as compared with the vehicle control group, there was no significant reduction in the sleep latency induced by sodium thiopental after intravenous injection of L- and racemic ornidazole. The sleep latency induced by sodium thiopental was significantly reduced by D-ornidazole. The reduction effect between L- and D-ornidazole was significantly different in the sleep latency induced by sodium thiopental. As compared with the vehicle control group, L-ornidazole did not significantly extend the duration of sleeping induced by sodium thiopental, while the duration of sleeping was significantly extended after administration of D- or racemic ornidazole. The duration of sleeping observed in the D-ornidazole group and racemic ornidazole group was significantly longer than that observed in the L-ornidazole group.

At a dose of 80 mg/kg, as compared with the vehicle control group, there was no significant reduction in the sleep latency induced by sodium thiopental after intravenous injection of L-ornidazole. The sleep latency induced by sodium thiopental was significantly reduced by D- and racemic ornidazole. The reduction effect between L- and D-ornidazole was significantly different in the sleep latency induced by sodium thiopental. As compared with the vehicle control group, the duration of sleeping induced by sodium thiopental was significantly extended after administration of L-, D- and racemic ornidazole. The duration of sleeping observed in the D-ornidazole group was significantly longer than that observed in the L-ornidazole group and racemic ornidazole group.

These results suggested that the boosting effect of L-ornidazole on sleeping induced by sodium thiopental was relatively weaker as compared with D-ornidazole and racemic ornidazole.

(4) The Effect of Intravenous Injection of L-Ornidazole on the Coordination of Balancing in Mice Experiments were conducted in 9 administration groups, L-, D- and racemic ornidazole were administered to them at doses of 40, 80 and 160 mg/kg. Positive control group received chlorpromazine at a dose of 3 mg/kg. The vehicle control group was administered the same volume of 0.9% sodium chloride injection containing propylene glycol. The injection volume was 0.2 ml/10 g, the administration rate was 0.2 ml/10 sec.

The results showed that no significant effect, as compared with the vehicle control group, at the same time-point, was shown on the coordination and balance in mice after intravenous injection of L-, D- and racemic ornidazole at doses of 40 and 80 mg/kg. There was no significant effect on the coordination and balance in mice after intravenous injection of 160 mg/kg L-ornidazole, but there was significant effect on the coordination and balance in mice after intravenous injection of 160 mg/kg D- and racemic ornidazole, respectively. The number of falling animals was significantly increased in these two groups.

The result suggested that L-ornidazole exhibited less inhibitory effect on the central nervous system as compared with D- or racemic ornidazole.

It was demonstrated, from the results obtained in the areas of toxicology, pharmacodynamics, and general pharmacology, that L-ornidazole exhibited lower toxicity and less central nervous inhibitory effects as compared with D- and racemic ornidazole, and that L-ornidazole was safer. In addition, the therapeutical efficacy for anti-anaerobic bacteria infection of L-ornidazole was slightly better or substantially the same as that of the racemic ornidazole.

The results showed that L-ornidazole exhibited lower toxicity and less central nervous inhibitory effects than D- or racemic ornidazole. Pharmacokinetics characteristics of L-ornidazole were superior to that of D- and racemic ornidazole, and pharmacodynamics of L-ornidazole was slightly better than or substantially the same as that of the racemic ornidazole. For these reasons, it would be more practicable to formulate L-ornidazole as anti-anaerobic bacteria infection drugs for clinical uses.

The present invention also provides pharmaceutical preparations which contain L-ornidazole as the active ingredient or the principal component. The pharmaceutical preparation includes oral preparation, such as tablets, capsules and granules; and intravenous preparations, such as small-volume infusion and large-volume infusion.

The oral preparations of the present invention can be achieved by the preparations having the following characteristics, that is, such oral preparations contain L-ornidazole as the active ingredient or the principal component, and additives as the adjuvants. The additives are at least one selected from disintegrating agent, binder, lubricant and filler. The dosage of the oral preparations according to the present invention is preferably 10~40 mg/kg/day, and more preferably 20-30 mg/kg/day.

The additives of the preparations according to the present invention may include disintegrating agents, binders, lubricants, fillers and mixtures thereof. Preferred fillers are pre-gelatinized□starch, starch, dextrin, sucrose, lactose, glucose, mannitol, microcrystalline cellulose, calcium sulfate, calcium carbonate, light magnesium oxide and mixtures thereof. Preferred lubricants are stearic acid, calcium stearate, magnesium stearate, talc powder, hydrogenated vegetable oil, polyethylene glycol, sodium laurylsulfate, magnesium laurylsulfate and mixtures thereof. Preferred disintegrating agents are croscarmellose sodium, crospovidone, starch, sodium starch glycolate, hydroxypropyl starch, low-substituted hydroxypropyl cellulose, polysorbate 80, sodium laurylsulfate and mixtures thereof. Preferred binders are hydroxylpropyl cellulose, povidone, starch slurry, dextrin, sucrose, syrup, 10%~20% gelatin solution, 10%~25% acacia solution, cellulose and its derivatives and the mixtures thereof.

L-ornidazole acting as the active ingredient in oral preparation is preferably 20~100%, more preferably 50~90%, even more preferably 60~80%, and most preferably 70~75%.

The additives in the oral preparation are preferably 0~80% w/w, more preferably 50~90%, even more preferably 60~80%, and most preferably 70~75%. The disintegrating agents in the oral preparations are preferably 0.5~5%, more preferably 0.8~2%, and most preferably 1.0~1.5%. The lubricants in oral preparations are preferably 0.3~1.0%, and more preferably 0.5~0.9%. The amount of the fillers is dependent on the specification of the preparation. And the amount of the binder is dependent on the fluidity and the disintegration of the granules in the actual production.

Detailed procedures for preparation are as follows:

The active ingredients and adjuvants were mixed thoroughly, followed by addition of blinders to prepare the damp mass, which was then subjected to granulating, drying, sizing, and directly packing to obtain the granular preparation. Alternatively, to the above mixtures were added the lubricants with thorough mixing, and followed by compression or capsule filling; or even directly undergo compression or capsule filling with the raw materials; tablets maybe coated or uncoated. Addition of disintegrating agent may be external, internal or internal-external.

The intravenous preparations of the present invention can be achieved by the preparation having the following characteristics, that is, such preparation contains L-ornidazole as the active ingredient or the principal component. Different forms of intravenous preparations can be obtained with the addition of different adjuvants. In the case that osmotic pressure regulator was added as the adjuvants, infusion preparation can be prepared. Preferred osmotic pressure regulators are sodium chloride, glucose, potassium gluconate, sodium gluconate, calcium gluconate, ferrous gluconate, magnesium gluconate, carboxyethyl starch, low molecular dextran, glycerin, sodium bicarbonate, potassium hydrogen phosphate, magnesium sulfate, calcium chloride, potassium chloride, sodium lactate, xylitol, sorbic acid, maltose, fructose and the mixtures thereof, in which sodium chloride, glucose and the mixtures thereof were more preferred. In the case organic solvent was used as the adjuvants, injection preparations can be prepared. Preferred organic solvents are propylene glycol, ethanol or polyethylene glycol, in which propylene glycol was more preferred. The preferred intravenous dosage was 5~40 mg/kg/day, and 10~20 mg/kg/day is more preferred.

Detailed preparation procedure is as follows:

a. Prescribed amount of L-ornidazole and the adjuvants were weighed, injection water was added, and then stirred till dissolved.

b. The pH was adjusted using the acid provided for intravenous infusion, injection water was added to the required volume. To the solution was added the activated carbon (for injection use), stirred well and left it to stand for 15 minutes, followed by decarburization with a titanium bar (5 μm). For further filtration, the solution was passed through the micro-void filter films of filter cartridge (preferably 0.45 μm and 0.22 μm).

c. Filling and sealing.

d. Sterilization.

The amount of the osmotic pressure regulator of the present invention can be obtained by calculation based on the isotonic principle. And the amount of the organic solvent is not less than 2% ml/mg (as compared with the amount of L-ornidazole).

The preparation process of the invention is practicable, and products exhibit reliable quality and excellent stability.

PREFERRED EMBODIMENTS OF THE INVENTION

The following examples are given for the purpose of illustrating the present invention and shall not be construed as being limitations on the scope or spirit of the instant invention.

Example 1

Formulation

| Ingredients | Quantity(mg/tablet) |
| --- | --- |
| L-ornidazole | 250 |
| Pre-gelatinized Starch | 80 |
| Sodium Starch Glycolate | 4 |
| Magnesium stearate | 3 |

For exemplification, 1000 tablets were prepared. Specifically, the active ingredient and the adjuvants were sieved through a 100-mesh sieve. Prescribed amount of L-ornidazole and pregelatinized starch were weighed and mixed thoroughly, followed by addition of 8% starch slurry to prepare the damp mass, which was then subjected to granulating, drying and sizing. To the dry granules were added prescribed amount of sodium starch glycolate and magnesium stearate. Subsequently, the granules were compressed and coated by 8% opadry in 95% ethanol solution.

Example 2

Formulation

| Ingredients | Quantity(mg/tablet) |
|---|---|
| L-ornidazole | 250 |
| Starch | 80 |
| Sodium Starch Glycolate | 4 |
| Magnesium stearate | 3 |

For exemplification, 1000 tablets were prepared. Specifically, the active ingredient and the adjuvants were sieved through a 100-mesh sieve. Prescribed amount of L-ornidazole and starch were weighed and mixed thoroughly, followed by addition of 6% aqueous povidone solution to prepare the damp mass, which was then subjected to granulating, drying and sizing. To the dry granules were added prescribed amount of talc powder and sodium starch glycolate, mixed thoroughly and compressed to obtain the tablets.

Example 4

Formulation

| Ingredients | Quantity(mg/capsule) |
|---|---|
| L-ornidazole | 250 |
| Starch | 45 |
| Magnesium stearate | 2 |

For exemplification, 1000 tablets were prepared. Specifically, the active ingredient and the adjuvants were sieved through a 100-mesh sieve. Prescribed amount of L-ornidazole and starch were weighed and mixed thoroughly, followed by addition of 6% starch slurry to prepare the damp mass, which was then subjected to granulating, drying and sizing. To the dry granules were added prescribed amount of magnesium stearate, mixed thoroughly and filled up the capsules.

Example 5

Formulation

| Ingredients | Quantity(mg/capsule) |
|---|---|
| L-ornidazole | 250 |
| Micron Silica Gel | 30 |
| Pre-gelatinized Starch | 50 |

For exemplification, 1000 capsules were prepared. Specifically, the active ingredient and the adjuvants were sieved through a 100-mesh sieve. Prescribed amount of L-ornidazole and pre-gelatinized starch were weighed and mixed thoroughly, followed by addition of 8% aqueous povidone solution to prepare the damp mass, which was then subjected to granulating, drying and sizing. To the dry granules were added prescribed amount of micron silica gel, mixed thoroughly and filled up the capsules.

Example 6

Formulation

| Ingredients | Quantity(mg/bag) |
|---|---|
| L-ornidazole | 250 |
| Mannitol | 250 |
| Sucrose | 200 |
| Sodium Starch Glycolate | 20 |

For exemplification, 1000 bags were prepared. Specifically, the active ingredient and the adjuvants were sieved through a 100-mesh sieve. Prescribed amount of L-ornidazole, mannitol, sucrose and sodium starch glycolate were weighed and mixed thoroughly, followed by addition of 8% starch slurry to prepare the damp mass, which was then subjected to granulating, drying, sizing, and packing.

Example 7

Formulation

| Ingredients | Quantity |
|---|---|
| L-ornidazole | 5 mg/ml |
| Sodium Chloride | 8.30 mg/ml |
| Injection Water (added up to) | 100 ml |

For exemplification, 100 bottles of L-ornidazole and sodium chloride injection were prepared. Specifically, prescribed amount of L-ornidazole and sodium chloride were weighed, followed by addition of 8 L injection water of 40° C., stirred and dissolved. The pH of the solution was adjusted to 4.0 by 0.1 mol/L hydrochloric acid, and the solution was added with injection water of 40° C. to the required total volume. Subsequently, to the resultant solution, 0.1% active carbon was added. The solution was stirred and left to stand for 15 minutes, followed by decarburization with a titanium bar (5 μm). For further filtration, the solution was passed through the microvoid filter films (0.45 μm and a 0.22 μm) of a filter cartridge. The resultant solution was filled and sealed in a 100 ml glass infusion bottle, which was then subjected to sterilization in a flowing stream of 100° C. for 45 minutes.

Example 8

Formulation

| Ingredients | Quantity |
|---|---|
| L-ornidazole | 2.5 mg/ml |
| Sodium Chloride | 8.60 mg/ml |
| Injection water (added up to) | 100 ml |

For exemplification, 100 bottles of L-ornidazole and sodium chloride injection were prepared. Specifically, prescribed amount of L-ornidazole and sodium chloride were weighed, followed by addition of 8 L injection water of 40° C., stirred and dissolved. The pH of the solution was adjusted to 4.5 by 0.1 mol/L citric acid, and the solution was added with injection water of 40° C. to the required total volume. Subsequently, to the resultant solution, 0.1% active carbon was added. The solution was stirred and left to stand for 15 minutes, followed by decarburization with a titanium bar (5 μm). For further filtration, the solution was passed through the microvoid filter films (0.45 μm and a 0.22 μm) of a filter cartridge. The resultant solution was filled and sealed in a 100 ml glass infusion bottle, which was then subjected to sterilization in a flowing stream of 100° C. for 45 minutes.

Example 9

Formulation

| Ingredients | Quantity |
|---|---|
| L-ornidazole | 1.25 mg/ml |
| Sodium Chloride | 8.80 mg/ml |
| Injection water (added up to) | 100 ml |

For exemplification, 100 bottles of L-ornidazole and sodium chloride injection were prepared. Specifically, prescribed amount of L-ornidazole and sodium chloride were weighed, followed by addition of 8 L injection water of 40° C., stirred and dissolved. The pH of the solution was adjusted to 3.5 by 0.1 mol/L lactic acid, and the solution was added with injection water of 40° C. to the required total volume. Subsequently, to the resultant solution, 0.2% active carbon was added. The solution was stirred and left to stand for 15 minutes, followed by decarburization with a titanium bar (5 μm). For further filtration, the solution was passed through the microvoid filter films (0.45 μm and a 0.22 μm) of a filter cartridge. The resultant solution was filled and sealed in a 100 ml glass infusion bottle, which was then subjected to sterilization in a flowing stream of 100° C. for 45 minutes.

Example 10

Formulation

| Ingredients | Quantity |
|---|---|
| L-ornidazole | 5 mg/ml |
| Glucose | 50 mg/ml |
| Injection water (added up to) | 100 ml |

For exemplification, 100 bottles of L-ornidazole and glucose injection were prepared. Specifically, prescribed amount of L-ornidazole and glucose were weighed, and dissolved in 8 L injection water of 45° C. The pH of the solution was adjusted to 3.5 by 0.1 mol/L hydrochloric acid, and the solution was added with injection water of 45° C. to the required total volume. Subsequently, to the resultant solution, 0.15% active carbon was added. The solution was stirred and left to stand for 15 minutes, followed by decarburization with a titanium bar (5 μm). For further filtration, the solution was passed through the microvoid filter films (0.45 μm and a 0.22 μm) of a filter cartridge. The resultant solution was filled and sealed in a 100 ml glass infusion bottle, which was then subjected to sterilization in a flowing stream of 100° C. for 45 minutes to give the L-ornidazole and glucose injection.

Example 11

Formulation

| Ingredients | Quantity |
|---|---|
| L-ornidazole | 5 mg/ml |
| Sodium Chloride | 4.2 mg/ml |
| Glucose | 25 mg/ml |
| Injection water (added up to) | 100 ml |

For exemplification, 100 bottles of L-ornidazole sodium chloride and glucose injection were prepared. Specifically, prescribed amount of L-ornidazole, sodium chloride and glucose were weighed, and dissolved in 8 L injection water of 40° C. The pH of the solution was adjusted to 4.5 by 0.1 mol/L tartaric acid, and the solution was added with injection water of 40° C. to the required total volume. Subsequently, to the resultant solution, 0.1% active carbon was added. The solution was stirred and left to stand for 15 minutes, followed by decarburization with a titanium bar (5 μm). For further filtration, the solution was passed through the microvoid filter films (0.45 μm and a 0.22 μm) of a filter cartridge. The resultant solution was filled and sealed in a 100 ml glass infusion bottle, which was then subjected to sterilization in a flowing stream of 100° C. for 45 minutes to give the L-ornidazole, sodium chloride and glucose injection.

Example 12

Formulation

| Ingredients | Quantity |
|---|---|
| L-ornidazole | 25 mg/ml |
| Propylene glycol | 0.5 ml/ml |
| Injection water (added up to) | 10 ml |

For exemplification, 100 bottles of L-ornidazole injection were prepared. Specifically, prescribed amount of L-ornidazole was weighed, and dissolved in propylene glycol of about 45° C., followed by addition of 100 mL injection water of 45° C. and stirred. The pH of the solution was adjusted to 4.5 by 0.1 mol/L hydrochloric acid. After dissolution, and the solution was added with injection water of 45° C. to the required total volume. Subsequently, to the resultant solution, 0.1% active carbon (for injection use) was added. The solution was stirred and left to stand for 15 minutes, followed by decarburization with a titanium bar (5 μm). For further filtration, the solution was passed through the microvoid filter films (0.45 μm and a 0.22 μm) of a filter cartridge. The resultant solution was filled and sealed in ampoule bottle, which was then subjected to sterilization in a flowing stream of 100° C. for 45 minutes to give the L-ornidazole injection.

The invention claimed is:
1. A method for treatment of diseases caused by anaerobic bacterial infections, comprising administering a pharmaceutical preparation consisting essentially of levo-ornidazole as the active ingredient to a patient in need of the treatment so as to reduce adverse events and toxicities of the patient's nervous system.

2. The method according to claim 1 wherein the reduction of adverse events and toxicities occurs to the nervous systems in an animal patient, when compared with an animal patient that is administered dextro-ornidazole and racemate ornidazole.

3. The method according to claim 1 wherein the reduction of adverse events and toxicities occurs to the nervous system in a human patient compared with a human patient that is administered with racemate ornidazole.

4. The method according to claim 1, wherein said pharmaceutical preparation is essentially free of dextro-ornidazole.

5. The method according to claim 1, wherein the levo-ornidazole is not converted to the dextro-ornidazole in vivo.

* * * * *